(12) United States Patent
Biedermann et al.

(10) Patent No.: US 7,591,839 B2
(45) Date of Patent: Sep. 22, 2009

(54) BONE ANCHORING ELEMENT FOR ANCHORING IN A BONE OR VERTEBRA, AND STABILIZATION DEVICE WITH SUCH A BONE ANCHORING ELEMENT

(75) Inventors: Lutz Biedermann, VS-Villingen (DE); Jürgen Harms, Karlsruhe (DE); Wilfried Matthis, Weisweil (DE)

(73) Assignee: Biedermann Motech GmbH, VS-Schwenningen (DE)

( * ) Notice: Subject to any disclaimer, the term of this patent is extended or adjusted under 35 U.S.C. 154(b) by 41 days.

(21) Appl. No.: 11/070,421

(22) Filed: Mar. 2, 2005

(65) Prior Publication Data

US 2005/0216003 A1 Sep. 29, 2005

Related U.S. Application Data

(60) Provisional application No. 60/550,009, filed on Mar. 3, 2004.

(30) Foreign Application Priority Data

Mar. 3, 2004 (DE) ........................ 10 2004 010 382

(51) Int. Cl.
*A61B 17/80* (2006.01)
(52) U.S. Cl. ........................ 606/266; 606/287
(58) Field of Classification Search .............. 606/61, 606/73
See application file for complete search history.

(56) References Cited

U.S. PATENT DOCUMENTS

| | | | | |
|---|---|---|---|---|
| 2,197,889 A | * | 4/1940 | Morris | 403/51 |
| 2,544,583 A | * | 3/1951 | Booth | 403/127 |
| 2,576,830 A | * | 11/1951 | Flumerfelt | 403/129 |
| 2,838,330 A | * | 6/1958 | Fidler | 403/126 |
| 2,855,232 A | * | 10/1958 | Kozak | 403/132 |
| 5,176,680 A | * | 1/1993 | Vignaud et al. | 606/61 |
| 5,443,527 A | * | 8/1995 | Wilson | 623/49 |
| 5,474,555 A | | 12/1995 | Puno et al. | 606/73 |
| 5,735,850 A | * | 4/1998 | Baumgartner et al. | 606/61 |
| 6,022,350 A | * | 2/2000 | Ganem | 606/61 |
| 6,623,485 B2 | * | 9/2003 | Doubler et al. | 606/61 |
| 6,716,214 B1 | * | 4/2004 | Jackson | 606/61 |
| 6,887,242 B2 | * | 5/2005 | Doubler et al. | 606/61 |
| 2002/0198527 A1 | | 12/2002 | Muckter | 606/73 |
| 2003/0040810 A1 | * | 2/2003 | Molino et al. | 623/52 |
| 2003/0109880 A1 | | 6/2003 | Shirado et al. | 606/61 |
| 2004/0006342 A1 | * | 1/2004 | Altarac et al. | 606/61 |
| 2004/0102781 A1 | * | 5/2004 | Jeon | 606/73 |

FOREIGN PATENT DOCUMENTS

| | | |
|---|---|---|
| EP | 0 669 109 B1 | 8/1995 |
| EP | 0 669 109 B1 | 5/1999 |
| EP | 1 273 269 A2 | 1/2003 |
| WO | WO 98/34554 | 8/1998 |

* cited by examiner

*Primary Examiner*—Eduardo C Robert
*Assistant Examiner*—Jerry Cumberledge
(74) *Attorney, Agent, or Firm*—Christie, Parker & Hale, LLP (57) ABSTRACT

A bone anchoring element comprises a bone anchoring element and a receiving member. The bone anchoring element can be in the form of a screw with a shaft and a first head. A second head is elastically connected to the first head. The second head is arranged in the receiving member such that the second head can swivel. The second head is fixed in the receiving member in an angular resting position. The screw is deflectable from the angular resting position relative to the second head. The second head is elastically connected to the first head such that a restoring force returns the screw to the angular resting position.

34 Claims, 6 Drawing Sheets

BONE ANCHORING ELEMENT FOR ANCHORING IN A BONE OR VERTEBRA, AND STABILIZATION DEVICE WITH SUCH A BONE ANCHORING ELEMENT

REFERENCE TO EARLIER FILED APPLICATIONS

The present invention claims the benefit of the filing date under 35 U.S.C. § 119(e) of U.S. Provisional Patent Application Ser. No. 60/550,009, filed Mar. 3, 2004, which is hereby incorporated by reference. The present application also claims foreign priority benefits pursuant to 35 U.S.C. § 119 (a)-(d) for German Patent Application 10 2004 010 382.8, filed Mar. 3, 2004 in Germany.

BACKGROUND

The present invention relates to a bone anchoring element for insertion into a bone or a vertebra that has a deflectable screw for dynamic stabilization. Further the present invention also relates to a stabilization device for such a bone anchoring element.

Conventional bone anchoring elements for the fixation of bone fractures or the stabilization of spinal columns typically consist of at least two screws anchored in a bone and/or a vertebra that are connected by a rigid plate or a rod. Because the screws are fixed relative to each other, the conventional bone anchoring elements are rigid and do not allow the bone and/or the vertebra to move.

In instances where dynamic stabilization is desired, the bone and/or the vertebra need to be stabilized such that the bone and/or the vertebra are capable of performing controlled, limited motion relative to each other. Dynamic stabilization may be obtained by using a flexible element instead of a rigid plate or rod to connect the screws, such as described in, for example, European Patent EP 0 669 109 B1 and U.S. Patent Publication No. 2003/0109880 A1. Because the screws are coupled by a flexible element, movement of one of the screws is transferred to the other screw through the flexible element. Due to the permanent cyclical partial load on the bone anchoring element, this transfer of movement can cause the screw to become loose in the bone and/or the vertebra, which can lead to separation of the screw from the bone and/or the vertebra.

Consequently, there is a need to uncouple the motion of the bone and/or the vertebra from the rod or the plate so that the bone anchoring elements remain securely anchored in the bone and/or the vertebra for the life of the patient. Moreover, there is a need to be able to optimally position the bone anchoring element relative to a rod or a plate connecting multiple bone anchoring elements.

One known way to achieve these needs is though a conventional polyaxial bone screw. One example of a polyaxial bone screw is described in U.S. Pat. No. 5,474,555. The polyaxial bone screw comprises a screw and a receiving member that is connecting to a rod. The screw is anchored in a bone and is connected to the receiving member such that the screw can swivel or pivot relative to the receiving member. The polyaxial bone screw that is described, however, does not allow for mutual stabilization of the bone and controlled partial motion thereof.

It is therefore desirable to develop a bone anchoring element for anchoring in a bone and/or a vertebra wherein the bone anchoring element allows controlled partial motion of the bone and/or vertebra that is to be stabilized, secure attachment to the bone and/or vertebra, and optimal positioning.

The foregoing paragraphs have been provided by way of general introduction and are not intended to limit the scope of the claims. The presently preferred embodiments together with further advantages will be best understood by reference to the following detailed description taken in conjunction with the accompanying drawings.

BRIEF SUMMARY

A bone anchoring element according to the invention comprises a bone anchoring element such as a screw and a receiving member. The screw has a shaft and a first head. A second head is elastically connected to the first head. The second head is arranged in the receiving member such that the second head can pivot or swivel. The second head is fixed in the receiving member in an angular resting position. The screw is deflectable from the angular resting position relative to the second head. The second head is elastically connected to the first head such that a restoring force returns the screw to the angular resting position.

A bone anchoring element is described in which the desired resting angular position of the shaft relative to the receiving part is adjustable.

DETAILED DESCRIPTION OF THE DRAWINGS AND PRESENTLY PREFERRED EMBODIMENTS

The invention and various embodiments thereof are presented in FIGS. 1 to 6 and the accompanying description wherein like numbered items are identical.

Figure 1:
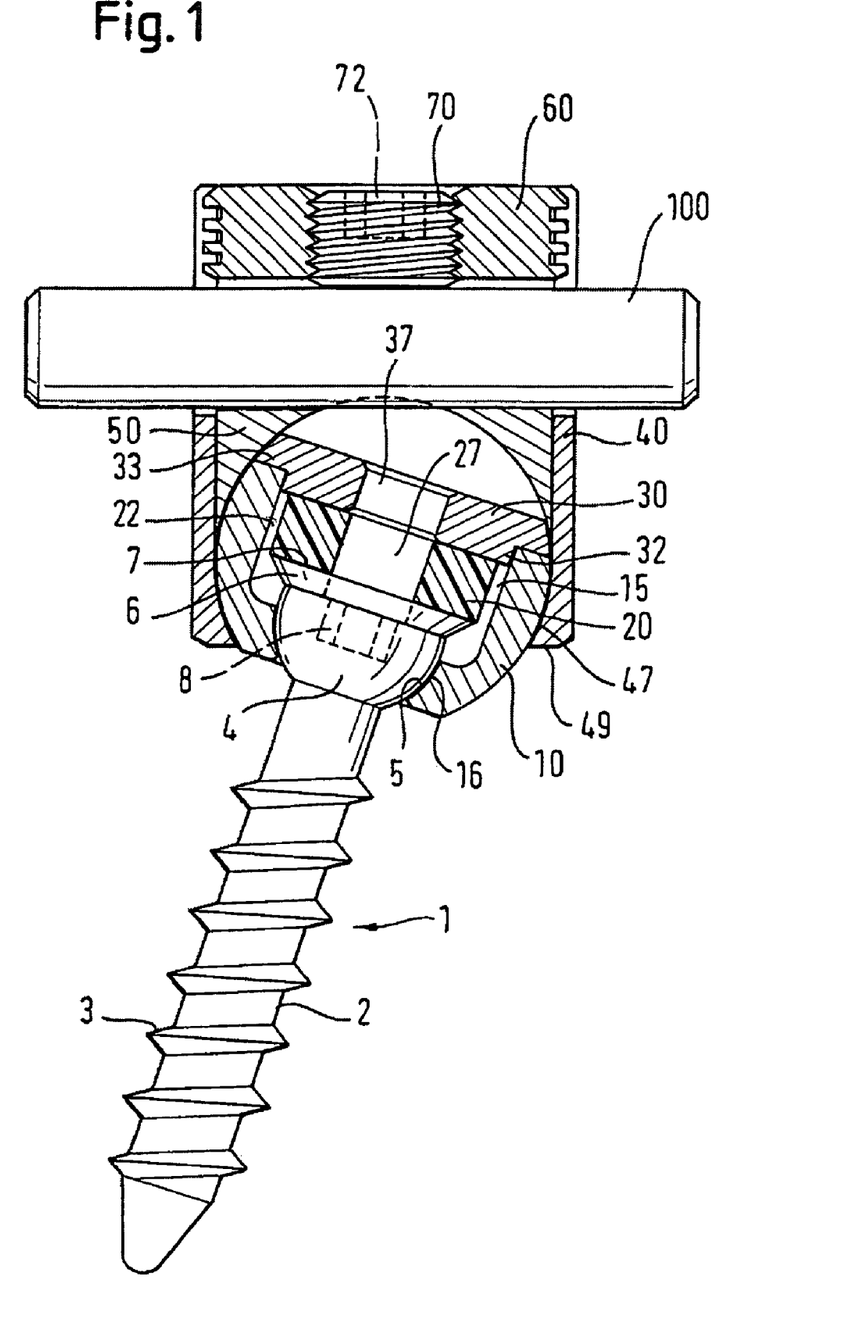
FIG. 1 is a partial sectional view of a bone anchoring element according to a first embodiment of the invention.
Figure 2:
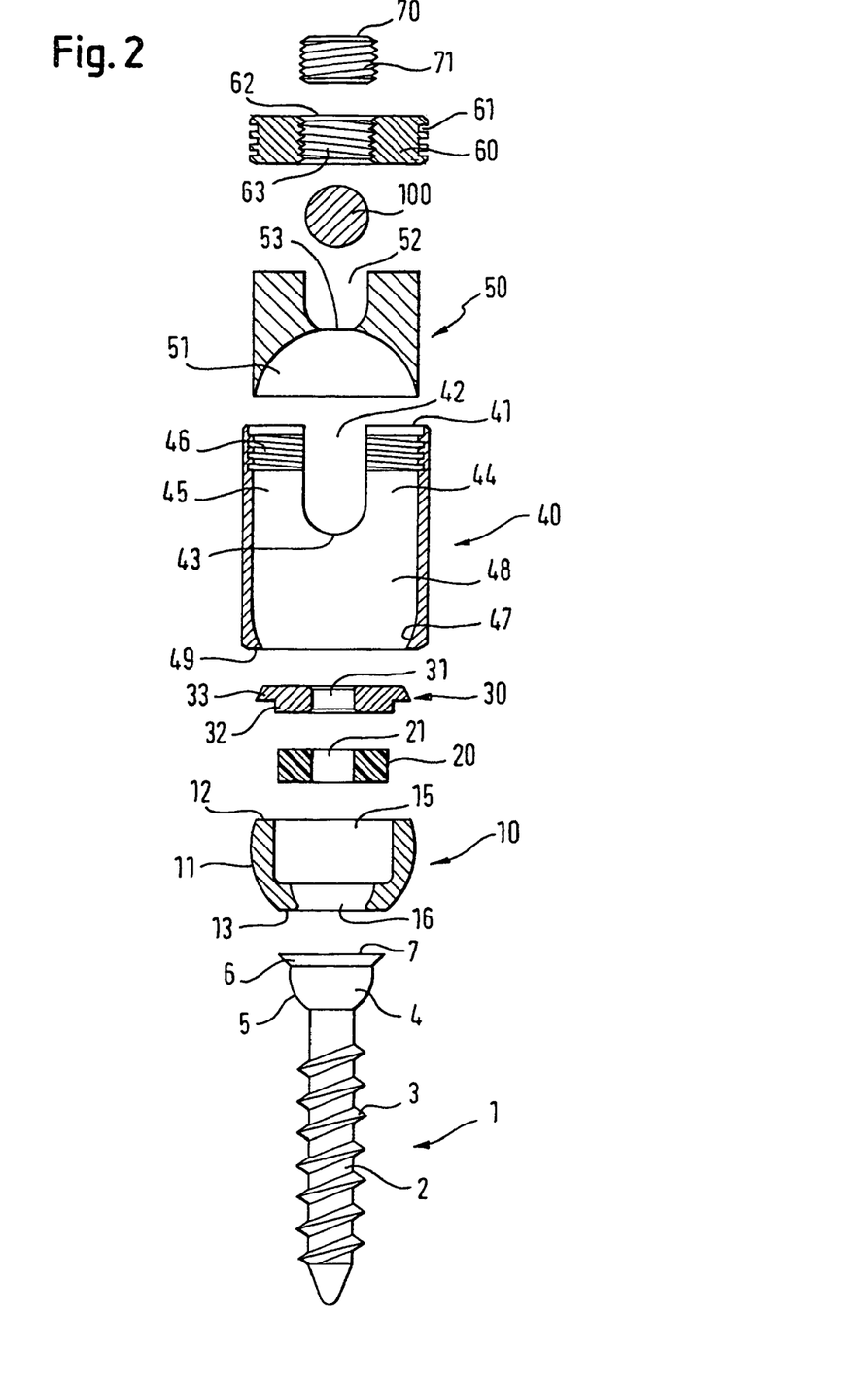
FIG. 2 is a partial sectional exploded view of the bone anchoring element according to the first embodiment.

FIGS. 1-2 show a bone anchoring element according to a first embodiment of the invention. In the illustrated embodiment, the bone anchoring element is shown as a polyaxial bone screw. As shown in FIG. 1, the bone anchoring element generally comprises a screw 1 having a shaft 2 with a bone thread 3. A first head 4 is connected to the shaft 2. A second head 10 receives the first head 4. A first pressure element 20 is arranged in the second head 10 adjacent to the first head 4 and is secured therein be a fastening cap 30. A receiving member 40 receives the second head 10. A second pressure element 50 is arranged in the receiving member 40. A first securing element 60 acts on the second pressure element 50 to secure the second head 10 in a desired angular resting position. A second securing element 70 acts on the rod 100 to secure the rod 100 in the receiving member 40. Although shown as a screw, it will be appreciated by those skilled in the art that the anchoring element can be any other type of anchoring element, including but not limited to a hook or a nail.

The bone anchoring element according to the first embodiment will now be described in greater detail. As shown in FIGS. 1-2, the first head 4 is connected to the shaft 2 and is provided in one piece therewith. Although the shaft 2 and the first head 4 are illustrated as being one piece, it will be appreciated by those skilled in the art that multiple pieces are also possible, for example, the shaft 2 and the first head 4 may be connected by press-fitting, an attachment member, such as a screw, etc. The first head 4 of the screw 1 comprises a substantially spherical outer surface 5 adjacent to the shaft 2. Although the first head 4 is illustrated as having a spherical outer surface 5, it will be appreciated by those skilled in the art that the first head 4 may be of any shape that enables the first head 4 to be held in the second head 10 such that the first head 4 is capable of swiveling or pivoting around the second head. The outer spherical surface 5 has a diameter larger than a diameter of the shaft 2. As shown in FIG. 1, on a side of the first head 4 facing away from the shaft 2, the first head 4 has a tool receiving recess 8 formed coaxially to an axis of the shaft 2. Although the tool receiving recess 8 is illustrated as having a substantially hexagonal-shape for receipt of a hex key (not shown), it will be appreciated by those skilled in the art that the tool receiving recess 8 may have any configuration corresponding to a desired tool, for example, the tool receiving recess 8 may have a cross-shape. As shown in FIG. 2, a widened edge or collar 6 is formed on a side of the first head 4 facing away from the shaft 2. The collar 6 forms a substantially level circular surface 7.

As shown in FIG. 2, the second head 10 has a partial spherical sleeve-shape. The second head 10 comprises a substantially spherical exterior surface 11, a first end 12, and a second end 13. Although the second head 10 is illustrated as having a substantially spherical exterior surface 11, it will be appreciated by those skilled in the art that the second head 10 may be of any shape that enables the second head 10 to swivel in the receiving member 40 while providing secure fixation therein. The first and second ends 12, 13 are arranged opposite to each other and are substantially level. A coaxial first bore 15 extends from the first end 12 toward the second end 13. The first bore 15 has a diameter larger than an outer diameter of the collar 6. A coaxial second bore 16 extends from the first bore 15 to the second end 13. The second bore 16 has a diameter adjacent to the second end 13 smaller than a diameter of the first head 4, but larger than the diameter of the shaft 2 such that the shaft 2 may be inserted there through. The diameter of the second bore 16 widens from the second end 13 towards the first bore 15 and is dimensioned such that the outer surface 5 of the first head 4 abuts an inner surface of the second bore 16. Adjacent to the first bore 15, the diameter of the second bore 16 is smaller than the diameter of the first head 4. Although the second bore 16 is illustrated as having a substantially spherical shape, it will be appreciated by those skilled in the art that the second bore 16 may be of any shape that enables the first head 4 to be held in the second head 10 such that the first head 4 is capable of swiveling.

As shown in FIG. 1, a first pressure element 20 is elastic and may be made, for example, from an elastomer. Body compatible elastomers can be used as elastomer material, e.g. but not limited to polyurethanes or polysiloxanes. First pressure element 20 is arranged on the circular surface 7 formed by the collar 6 of the first head 4. Alternatively, the first pressure element 20 may be, for example, one or more appropriately arranged springs. Preferably, the first pressure element 20 is shaped substantially like a disc and has a circular cross-section and a predetermined thickness. As shown in FIGS. 1-2, the first pressure element 20 has a coaxial pressure element bore 21 that communicates with the tool receiving recess 8 of the first head 4. The first pressure element 20 may have an outer diameter dimensioned such that a gap 22 is formed between the first pressure element 20 and a lateral wall of the first bore 15 when the first pressure element 20 is inserted therein, as shown in FIG. 1. The gap 22 accounts for elastic deformation of the first pressure element 20.

A rigid fastening cap 30 is arranged on a side of the first pressure element 20 facing away from the collar 6 of the first head 4. As shown in FIG. 2, the rigid fastening cap 30 is shaped substantially like a disc and has a coaxial fastening cap bore 31 that communicates with the coaxial pressure element bore 21. The fastening cap 30 has a first section 32 and a second section 33. The first section 32 faces the first pressure element 20. The first section 32 has an outer diameter corresponding to or slightly smaller than the inner diameter of the first bore 15 such that the fastening cap 30 may be inserted into and fixed to the second head 10, for example, by press-fitting. Although the fastening cap 30 is illustrated as being fixed to the second head 10 by press-fitting, it will be appreciated by those skilled in the art that other known methods may be used to fix the fastening cap 30 to the second head 10, for example, the fastening cap 30 may be provided with an outer thread that engages an internal thread of the first bore 15 in an area adjacent to the first end 12. The second section 33 faces away from the first pressure element 20. The second section 33 has an outer diameter larger than the outer diameter of the first section 32. The second section 33 engages the first end 12 of the second head 10 to form a stop when the first section 32 is inserted in the first bore 15. The second section 33 has a substantially spherical external surface that forms an extension of the exterior surface 11 of the second head 10.

As shown in FIG. 2, the receiving member 40 is substantially cylindrical in shape and has a coaxial receiving member bore 48 extending from a first side 41 toward a second side 49. The receiving member bore 48 has a diameter larger than the outer diameter of the second head 10. Adjacent to the second side 49 is a narrowed portion 47 that has a diameter that spherically tapers from the first receiving member bore 48 to the second end 49 such that the second head 10 may be swiveled in a predetermined angular range when positioned in the receiving member 40. The narrowed portion may have any shape such as spherical, conical, or otherwise tapering towards the second side to allow second head 10 to swivel. A cut-out 42 extends from the first side 41 toward the second side 49 of the receiving member 40. The cut-out 42 has a substantially U-shaped cross-section and is dimensioned to be just large enough that a rod 100 may be inserted therein. The cut-out 42 has a base 43. The cut-out 42 forms first and second legs 44, 45, respectively. The first and second legs 44, 45 have free ends with internal threads 46.

The second pressure element 50 is arranged in the receiving member 40 toward the first side 41. The second pressure element 50 is substantially cylindrically symmetrical in shape and has an outer diameter smaller than the diameter of the first receiving member bore 48 such that the second pressure element 50 may be inserted into the first bore 48. The second pressure element 50 has a bottom side 51 that faces the second head 10. The bottom side 51 has a substantially concave surface having a radius corresponding to the radius of the second head 10 and the fastening cap 30 fixed thereto. Although the bottom side 51 is illustrated as having a substantially concave surface, it will be appreciated by those skilled in the art that the bottom side 51 may be of any shape that enables the second head 10 to swivel in the receiving member 40 and provides secure fixation of the second head 10 therein. On a side facing away from the second head 10, the second pressure element 50 has a slot 52 with a U-shaped cross-section and a bottom surface 53. The bottom surface 53 has a radius slightly larger than the radius of the rod 100. The second pressure element 50 has a coaxial second pressure element bore (not shown) corresponding to the fastening cap bore 37 for receiving the screwing tool (not shown).

As shown in FIG. 2, the first securing element 60 comprises a coaxial securing element bore 62. The securing element bore 62 is provided with interior threads 63. An outer surface of the first securing element 60 is provided with outer threads 61 corresponding to the internal threads 46 of the receiving member 40. A tool receiving opening (not shown) is formed on a side facing away from the pressure element 50 for receiving the screwing tool (not shown).

As shown in FIG. 1, the second securing element 70 has a tool receiving aperture 72 for receiving the screwing tool (not shown). Although the tool receiving aperture 72 is illustrated as having a substantially hexagonal-shape for receipt of a hex key (not shown), it will be appreciated by those skilled in the art that the tool receiving aperture 72 may have any configuration corresponding to a desired tool, for example, the tool receiving aperture 72 may have a cross-shape. An outer surface of the second securing element 70 is provided with exterior threads 61 corresponding to the interior threads 63 of the coaxial securing element bore 62.

During assembly, the shaft 2 of the screw 1 is inserted into the first end 12 of the second head 10 and guided through the second end 13 of the second head 10 until the first head 4 is received in the second bore 16 and the outer surface 5 of the first head 4 engages the inner surface of the second bore 16. The first pressure element 20 is inserted into the second head 10 and positioned adjacent to the circular surface 7 of the collar 6. The fastening cap 30 is attached to the second head 10 by inserting the first section 31 of the fastening cap into the first bore 15. The fastening cap 30 engages the first pressure element 20. The first pressure element 20 has a thickness such that the fastening cap 30 exerts pressure on the first pressure element 20 when the fastening cap 30 is inserted into the first bore 15. As a result of the pressure of the fastening cap 30, the first pressure element 20 exerts pressure on the circular surface 7 of the collar 6, which causes the outer surface 5 of the first head 4 to press against the inner surface of the second bore 16 to elastically secure the screw 1 in the second head 10. The frictional forces between the outer surface 5 of the first head 4 and the second bore 16 may be optimized and/or improved with a glide coating, a glide foil or a glide ring.

The second head 10, which is attached to the screw 1, is inserted into the receiving member bore 48 of the receiving member 40 until the second head 10 is positioned adjacent to the second side 49. The bottom side 57 of the second pressure element 50 is inserted into the receiving member bore 48 of the receiving member 40 until the bottom side 57 of the second pressure element 50 is positioned adjacent to the second head 10 and the slot 52 aligns with the cut-out 42. The screwing tool (not shown) is inserted through the second pressure element bore (not shown), the fastening cap bore 37, the pressure element bore 27, and into the tool receiving recess 8 of the screw 1. The screw 1 is screwed into a bone (not shown) or vertebra (not shown) with the screwing tool (not shown).

The rod 100 is inserted into the cut-out 42 and the slot 52, and the position of the receiving member 40 relative to the second head 10 is adjusted to the desired angular resting position. To fix the second head 10 in the desired angular resting position, the outer threads 61 of the first securing element 60 are engaged with the internal threads 46 of the first and second legs 44, 45 of the receiving member 40. The first securing element 60 is tightened until the first securing element 60 engages the second pressure element 50 and applies pressure thereto. The second pressure element 50 has a height in a direction of a cylindrical axis of the receiving member 40 so that by tightening the first securing element 60, the first securing element 60 applies pressure to the second pressure element 50. The second pressure element 50 thereby applies pressure to the fastening cap 30 and the second head 10 to secure the second head 10 in the angular resting position. The pressure applied to the fastening cap 30 further secures the fastening cap 30 to the second head 10. This arrangement makes it possible to align and subsequently pre-fix the second head 10 relative to the receiving member 40.

The exterior threads 77 of the second securing element 70 are then engaged with the interior threads 63 of the first securing element 60. As the second securing element 70 is tightened, the rod 100 is secured in the cut-out 42 of the receiving member 40 by the second securing element 70 and the bottom surface 53. Simultaneously, by tightening the second securing element 70, the rod 100 presses against the bottom surface 53 of the slot 52, which exerts pressure on the second pressure element 50 and thus the second head 10 to further secure the second head 10 in the angular resting position. The first and second securing elements 60, 70 thereby allow the second head 10 and the rod 100 to be independently fixed. Alternatively, a single securing element may be used to fix the rod 100 and the screw 1, wherein the single securing element would exert pressure onto the second pressure element 50 and thereby onto the second head 10 through the rod 100.

Figure 3A:
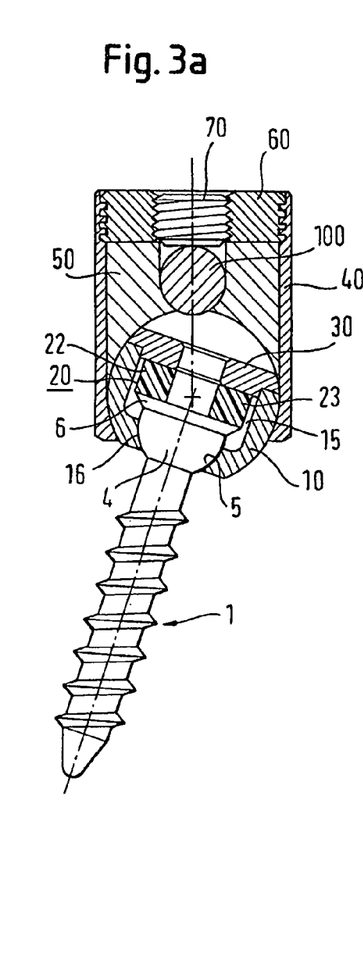
FIG. 3a is a partial sectional view schematically illustrating the bone anchoring element of the first embodiment in an angular resting position.
Figure 3B:
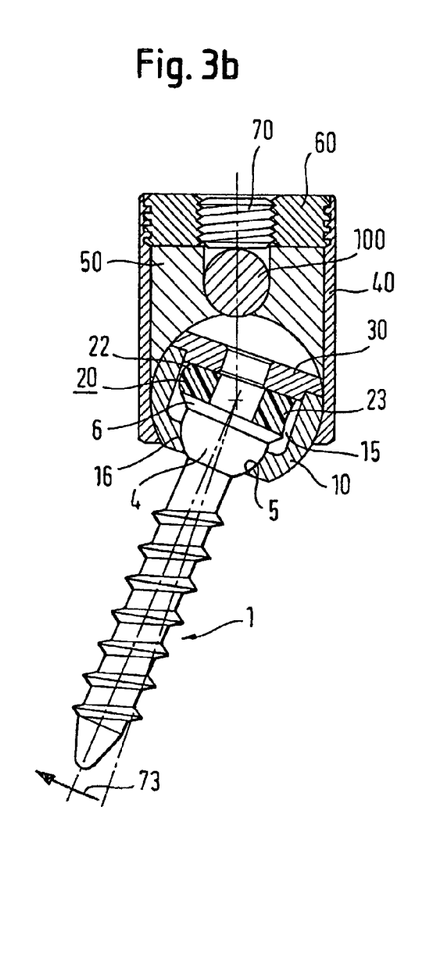
FIG. 3b is a partial sectional view schematically illustrating the bone anchoring element of the first embodiment deflected a first direction from the angular resting position.
Figure 3C:
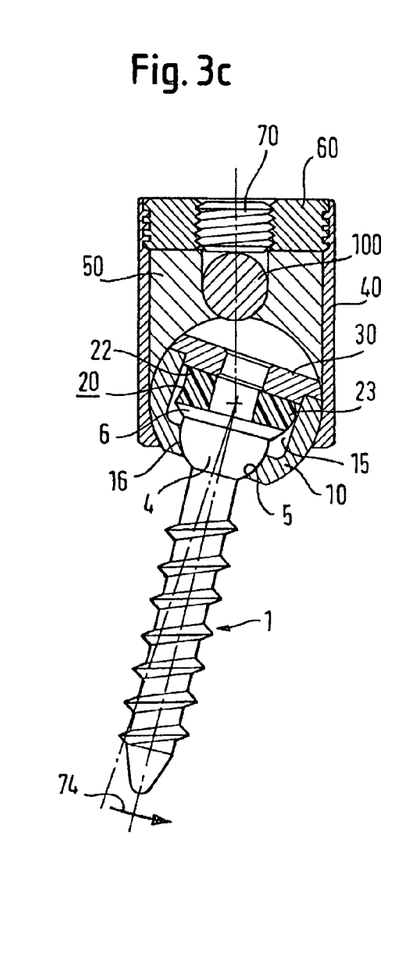
FIG. 3c is a partial sectional view schematically illustrating the bone anchoring element of the first embodiment deflected a second direction from the angular resting position.

FIGS. 3a to 3c schematically illustrate the operation of the bone anchoring element of the first embodiment. FIG. 3a shows the screw 1 in the angular resting position, and FIGS. 3b-3c show the screw 1 deflected from the angular resting position in a direction indicated by arrows 73, 74. As shown in FIG. 3a, a first side 22 and a second side 23 opposite the first side 22 of the first pressure element 20 have an even thickness in the angular resting position. As shown in FIG. 3b, a deflection of the screw 1 in the direction indicated by the arrow 73 causes the first side 22 of the first pressure element 20 to compress and the second side 23 of the first pressure element 20 to stretch. This elastic deformation of the first pressure element 20 causes internal tension therein, which exerts a restoring force acting against the deflection so that the screw 1 is forced to return to the angular resting position. As shown in FIG. 3c, a deflection of the screw 1 in the direction indicated by the arrow 74 causes the second side 23 of the first pressure element 20 to compress and the first side 22 of the first pressure element 20 to stretch. This elastic deformation of the first pressure element 20 causes internal tension therein, which exerts a restoring force acting against the deflection so that the screw 1 is forced to return to the angular resting position. The deflection of the screw 1 is thereby decoupled from the possibility of adjustment of the angular resting position, by the first head 4, the second head 10, and the receiving member 40.

Thus, upon motion of the bone (not shown) or vertebra (not shown) from the angular resting position, the first pressure element 20 exerts a restoring force onto the bone (not shown) or vertebra (not shown), which returns the screw 1 to the angular resting position and thus limits the motion of the bone (not shown) or vertebra (not shown). The elastic connection of the first and second heads 4, 10 allow the bone anchoring element to receive axial forces acting in a direction of the axis of the shaft 2, as well as flexural and torsional forces. Torque acting on the bone (not shown) or vertebra (not shown) via the shaft 2 is thereby blocked and the bone anchoring element is prevented from coming loose because of the permanent cyclic partial load on the anchoring.

The amount of deflection from the angular resting position is limited by the ratio of the diameter of the collar 6 of the screw 1 to the inner diameter of the first bore 15 of the second head 10. The amount of deflection can therefore be varied by using various size ratios for the diameter of the collar 6 and the inner diameter of the first bore 15. Additionally, the magnitude of the restoring force may be changed by altering, for example, the thickness of the first pressure element 20, the choice of material used for the first pressure element 20, and/or the shape of the first pressure element 20. The flexibility of the bone anchoring element can therefore be limited to a desired amount with respect to axial forces, flexural forces, and torsional forces.

Figure 4:
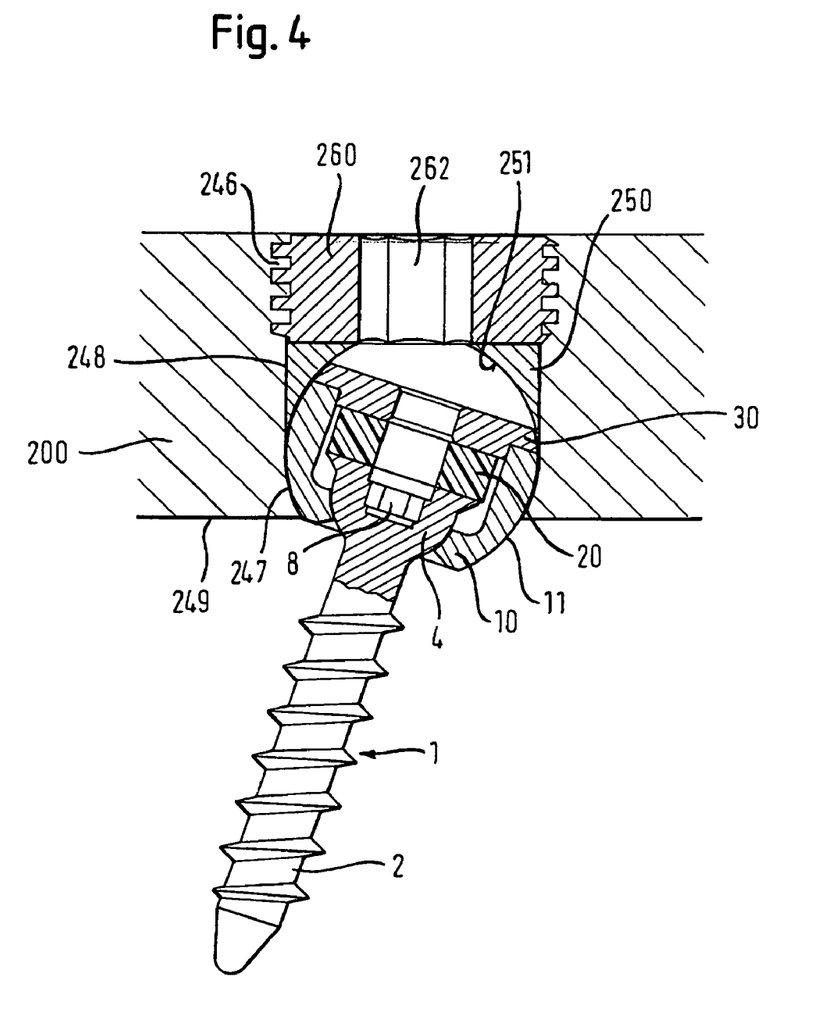
FIG. 4 is a partial sectional view of a bone anchoring element according to a second embodiment of the invention.

FIG. 4 shows a bone anchoring element according to a second embodiment of the invention. Elements of the second embodiment that are identical to elements of the first embodiment will be referenced using the same reference numerals and will not be described hereafter.

The bone anchoring element of the second embodiment includes a plate 200 instead of the receiving member 40 and the rod 100. A first plate bore 248 extends from a first side of the plate 200 toward a second side 249 of the plate 200. The first plate bore 248 has a diameter larger than the outer diameter of the second head 10. Adjacent to the first side of the plate 22, the first plate bore 248 has internal threads 246. Adjacent to the second end 249 of the plate 200 and coaxial to the first plate bore 248 is a second plate bore 247. The second plate bore 247 has a diameter that spherically tapers from the diameter of the first plate bore 248 towards the second end 249. The second head 10 is thereby held in the plate 200 by the second plate bore 247 and is capable of swiveling in a predetermined angular range, similar to the first embodiment.

A second pressure element 250 is arranged in the first plate bore 248 toward the first side. The second pressure element 250 is substantially cylindrically symmetric in shape and has an outer diameter smaller than the diameter of the first plate bore 248 such that the second pressure element 250 may be inserted into the first plate bore 248. The second pressure element 250 has a bottom side 251 that faces the second head 10. The bottom side 251 has a substantially concave surface and a radius corresponding to the radius of the second head 10 and the fastening cap 30 fixed thereto. The second pressure element 250 has a coaxial second pressure element bore (not shown) for receiving the screwing tool (not shown).

A securing element 260 has a coaxial securing element bore 262 for receiving a screwing tool (not shown). The securing element bore 262 has a cross-section such that the screwing tool (not shown) that is to be received in the tool receiving recess 8 of the first head 4 can reach there through. Although the securing element bore 262 is illustrated as having a substantially hexagonal-shape for receipt of a hex key (not shown), it will be appreciated by those skilled in the art that the securing element bore 262 may have any configuration corresponding to a desired tool. The securing element 260 has outer threads corresponding to the internal threads 246.

Unlike the first embodiment, the bone anchoring element of the second embodiment can be completely preassembled, because the screwing tool (not shown) may be inserted through the securing element bore 262, the second pressure element bore (not shown), the fastening cap bore 37, and the pressure element bore 27 and into the tool receiving recess 8 of the screw 1 while the securing element 260 is loosely attached to the plate 200. Subsequently, the angular resting position of the plate 200 relative to the shaft 2 may be adjusted and the securing element 260 tightened. The second pressure element 250 has a height in a direction of the first plate bore 248 dimensioned such that by tightening the securing element 260 into the internal threads 246 of the first plate bore 248, pressure is exerted onto the second pressure element 250. The second pressure element 250 exerts pressure on the second head 10 to fix the second head 10 in the plate 200 in the angular resting position. The plate 200 is therefore simultaneously connected to the screw 1 as the first head 10 is secured. This arrangement makes it possible to align and subsequently pre-fix the second head 10 relative to the plate 200.

Figure 5:
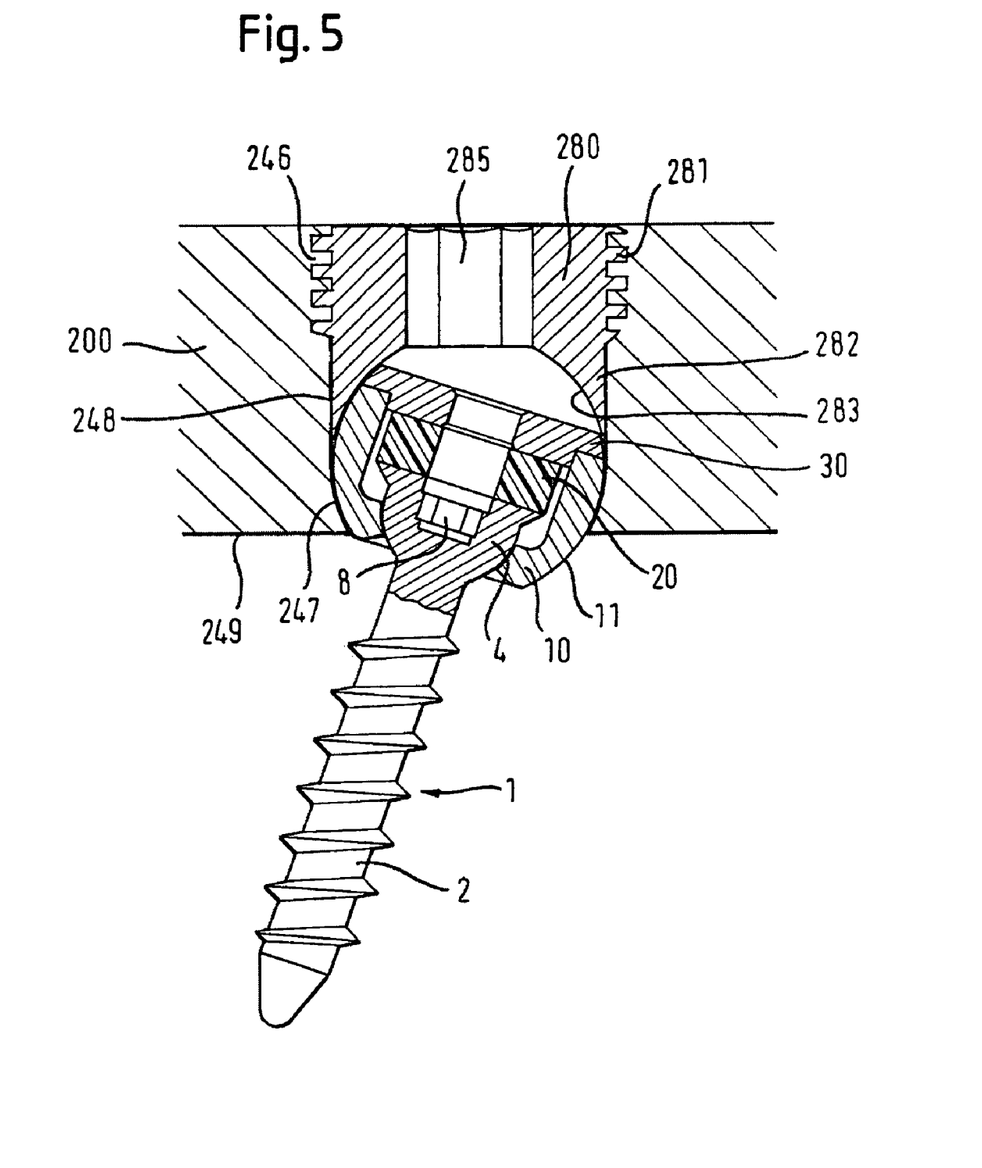
FIG. 5 is a partial sectional view of a bone anchoring element according to a third embodiment of the invention.

FIG. 5 shows a bone anchoring element according to a third embodiment of the invention. Elements of the third embodiment that are identical to elements of the second embodiment will be referenced using the same reference numerals and will not be described hereafter.

The bone anchoring element of the third embodiment differs from the bone anchoring element of the second embodiment in that the second pressure element 250 and the securing element 260 are formed in one piece in the form of a securing member 280. The securing member 280 has a first section 281 with outer threads for screwing into the internal threads 246 of the first plate bore 248. Adjacent to the first section 281 and on a side facing the second plate bore 247, the securing member 280 has a second section 282. The second section 282 is essentially cylindrically symmetrical in shape and has an outer diameter that is smaller than the diameter of the first plate bore 248 so that the securing member 280 may be screwed into the first plate bore 248. The securing member 280 has a bottom side 283 that faces the second head 10. The bottom side 283 has a substantially concave surface having a radius corresponding to the radius of the second head 10 and the fastening cap 30 fixed thereto. The securing member 280 has a coaxial securing member bore 285. The securing member bore 285 has a cross-section such that the screwing tool (not shown) that is to be received in the tool receiving recess 8 of the first head 4 can reach there through. Although the securing member bore 285 is illustrated as having a substantially hexagonal-shape for receipt of a hex key (not shown), it will be appreciated by those skilled in the art that the securing member bore 285 may have any configuration corresponding to a desired tool.

Similar to the second embodiment, the bone anchoring element of the third embodiment can be completely preassembled, because the screwing tool (not shown) may be inserted through the securing member bore 285, the fastening cap bore 37, and the pressure element bore 27 and into the tool receiving recess 8 of the screw 1 while the securing member 280 is loosely attached to the plate 200. The securing member 280 has a height in a direction of the first plate bore 248 dimensioned such that by tightening the securing member 280, the bottom side 283 exerts pressure onto the second head 10. The pressure exerted on the second head 10 by the bottom side 283 of the securing member 280 secures the second head 10 in the angular resting position. The angular resting position may be adjusted at the time of tightening of the securing member 280. The plate 200 is therefore simultaneously connected to the screw 1 as the first head 10 is secured. This arrangement makes it possible to align and subsequently pre-fix the second head 10 relative to the plate 200.

Figure 6:
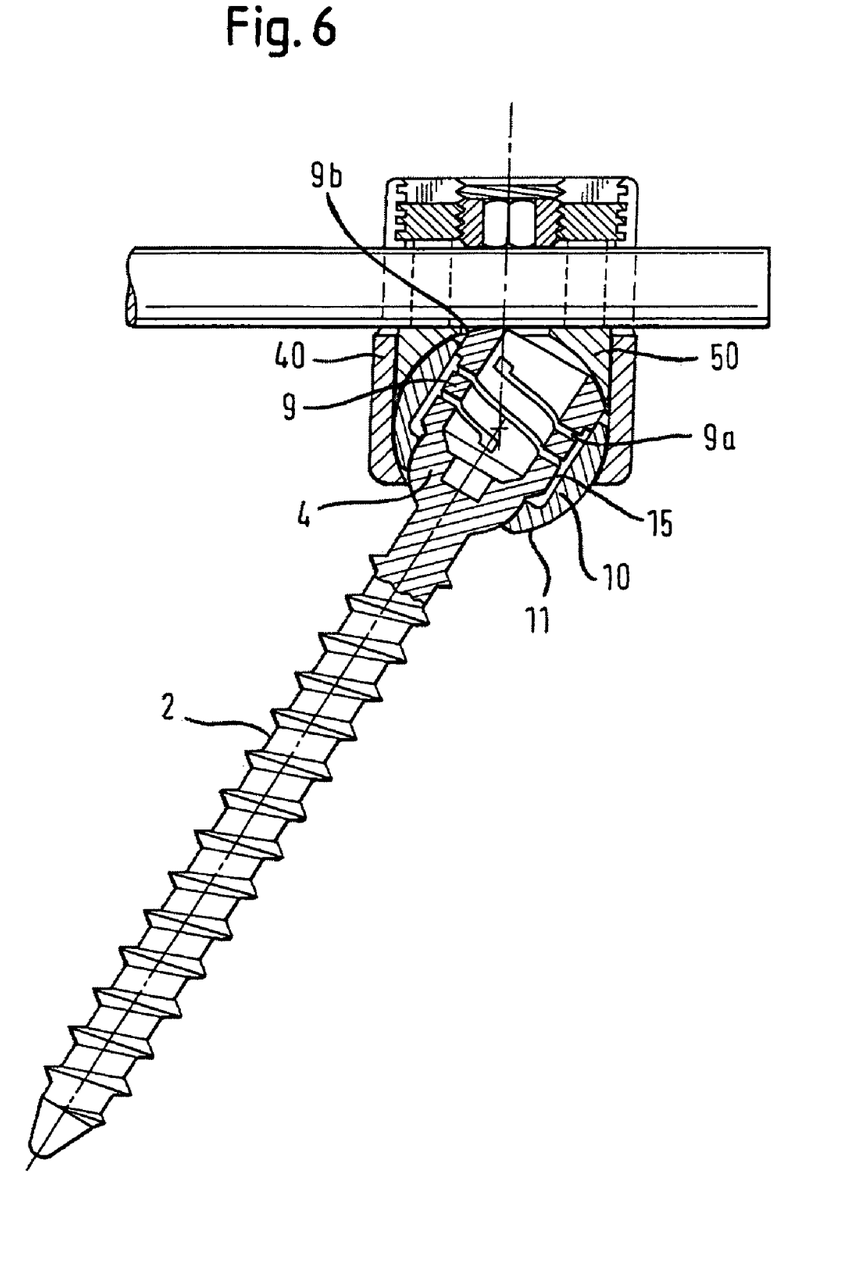
FIG. 6 is a partial sectional view of a bone anchoring element according to a fourth embodiment of the invention.

FIG. 6 shows a bone anchoring element according to a fourth embodiment of the invention. Elements of the fourth embodiment that are identical to elements of the first embodiment will be referenced using the same reference numerals and will not be described hereafter.

In the fourth embodiment, an elastic first pressure element 9 is integrally formed with the first head 4. The elastic first pressure element 9 has a substantially hollow cylindrical shape and extends coaxially to the axis of the shaft 2. The elastic pressure element 9 extends from the collar 6 of the first head 4 on a side of the collar 6 facing away from the shaft 2 toward the second pressure element 50. On a side of the first pressure element 9 facing away from the collar 6, the first pressure element 9 has a holding portion 9b having a larger outer diameter than the remainder of the first pressure element 9. The holding portion 9b secures the first head 4 in the first bore 15 of the second head 10. A top surface of the holding portion 9b that faces the second pressure element 50 has a substantially spherical outer surface that forms an extension of the exterior surface 11 of the second head 10. Circumferential recesses 9a are formed in the first pressure element 9. The circumferential recesses 9a are shaped such that the first pressure element 9 forms a substantially helical spring extending parallel to the axis of the shaft 2.

The bone anchoring element according to the fourth embodiment is assembled and operates in substantially the same manner as the bone anchoring element according to the first embodiment. In the fourth embodiment, the second head 10 is fixed in the angular resting position in the receiving member 40 by pressure exerted on the first pressure element 9 and the second head 10 by the second pressure element 50. When the screw 1 is deflected from the angular resting position, the circumferential recesses 9a of the first pressure element 9 cause the first pressure element 9 to elastically deform. Because the first pressure element 9 is in the form of a substantially helical spring extending parallel to the axis of the shaft 2, one side of the first pressure element 9 is compressed and another side of the first pressure element 9 is stretched when the screw 1 is deflected. This elastic deformation of the first pressure element 9 causes internal tension therein, which exerts a restoring force acting against the deflection so that the screw 1 is forced to return to the angular resting position. The magnitude of the restoring force may be changed by altering the size, length, etc. of the circumferential recesses 9a to limit the flexibility of the bone anchoring element to a desired amount.

All of the embodiments of the bone anchoring element described herein are firmly anchored in the bone (not shown) and/or the vertebra (not shown) while limiting mobility of the bone (not shown) and/or the vertebra (not shown) such that there is an increase in cyclical partial load, which stimulates the growth of bone. The bone anchoring elements may be used, for example, in a stabilization device comprising at least one bone anchoring element as described herein in combination with a rod or plate and a second bone anchoring element.

The elastic properties of the bone anchoring element of the instant invention are easy to implement during manufacture by changing the dimensions of the first head part, the second head part, the elastic pressure element and/or the material used for the elastic pressure element.

The foregoing illustrates some of the possibilities for practicing the invention. Many other embodiments are possible within the scope and spirit of the invention. For example, two or more of the bone anchoring elements may be used in combination with a rod or with a plate, and, similarly, the bone anchoring elements can be combined with known bone anchoring elements, such a bone screws or hooks. Additionally, other implementations of the bone anchoring elements are possible, such as use as receiving parts and fixation devices, wherein it is crucial for the shaft to be capable of elastic deflection from an angular resting position and for the adjustment of the angular resting position to be uncoupled from any elastic deformation. It is also possible to combine elements of one or more of the embodiments with elements of another embodiment. It is, therefore, intended that the foregoing description be regarded as illustrative rather than limiting, and that the scope of the invention is given by the appended claims together with their full range of equivalents.

We claim:

1. A bone anchoring device, comprising:
   a bone anchoring element having a shank with a first head directly fixed to the shank;
   a receiving member having a recess;
   a second head in the recess of the receiving member and pivotally arranged relative to the receiver member, the first head located in the second head;
   at least one securing element configured to fix the second head from pivoting in the recess of the receiving member; and
   an elastic pressure element configured to pivotally couple the anchoring element, including the first head and the shank, and the second head between a first position and a plurality of second positions angularly offset from the first position;
   wherein when the second head is fixed from pivoting in the recess of the receiver member, the first head and the shank are together pivotable relative to the second head between the first position and the plurality of second positions with the elastic pressure element biasing the first head and the shank from the plurality of second positions wherein the elastic pressure element is compressed on one side more than an opposite side to the first position wherein the compressive forces exerted on the elastic pressure element are balanced to provide a resting position of the first head and the shank in the first position.

2. The bone anchoring device according to claim 1, wherein the pivoting of the bone anchoring element is decoupled from the fixation of the second head when the second head is fixed from pivoting.

3. The bone anchoring device according to claim 1, wherein the first head is elastically connected to the second head by the pressure element.

4. The bone anchoring device according to claim 1, wherein the pressure element acts on the first head to secure the first head in the second head.

5. The bone anchoring device according to claim 1, wherein the pressure element is made of an elastomer.

6. The bone anchoring device according to claim 1, wherein the pressure element is made of one or more springs.

7. The bone anchoring device according to claim 1, wherein the pressure element is integrally formed with the first head.

8. The bone anchoring device according to claim 1, wherein the pressure element has circumferential recesses.

9. The bone anchoring device according to claim 1, further comprising a second pressure element acting on the second head that fixes the second head from pivoting in a fixed position.

10. The bone anchoring device according to claim 9, wherein the second pressure element has a bottom surface corresponding to an exterior surface of the second head.

11. The bone anchoring device according to claim 9, wherein the at least one securing element secures the second pressure element in the receiving member and applies pressure thereto.

12. The bone anchoring device according to claim 1, wherein the second head has first and second bores, the first head being arranged in the first and second bores such that the first head can swivel.

13. The bone anchoring device according to claim 1, wherein the receiving member has a narrowed portion for securing the second head therein.

14. The bone anchoring device according to claim 1, wherein the receiving member is a plate.

15. The bone anchoring device according to claim 1, wherein the receiving member has a cut-out for receiving a rod.

16. The bone anchoring device according to claim 15, further comprising a rod.

17. A bone anchoring device according to claim 1, wherein said anchoring element comprises a screw.

18. A bone anchoring device according to claim 1, wherein said anchoring element comprises a hook.

19. A bone anchoring device comprising:
a screw with a shaft and a first head directly fixed to the shaft;
a receiving member having a recess;
a second head in the recess of the receiving member and pivotably arranged relative to the receiving member, the second head having a bore, the first head being positioned in the bore such that the first head abuts an inner surface of the bore, the first head configured to be pivotable in the second head;
a second pressure element configured to fix the second head from pivoting in the recess of the receiving member; and
a first pressure element being elastically deformable and configured to pivotally couple the first head and the second head between a first position and a plurality of second positions angularly offset from the first position;
wherein the first pressure element biases the first head from the plurality of second positions to the first position;
wherein the first pressure element is made from a material being more elastic than a material of the first head.

20. The bone anchoring device according to claim 19, wherein the pivoting of the screw is decoupled from the fixation of the second head when the second head is fixed from pivoting.

21. The bone anchoring device according to claim 19, wherein the first pressure element acts on the first head to secure the first head in the second bore.

22. The bone anchoring device according to claim 19, wherein the first pressure element is made of an elastomer.

23. The bone anchoring device according to claim 19, wherein the first pressure element is integrally formed with the first head.

24. The bone anchoring device according to claim 19, wherein the first pressure element has circumferential recesses.

25. The bone anchoring device according to claim 19, wherein the second pressure element has a bottom surface corresponding to an exterior surface of the second head.

26. The bone anchoring device according to claim 19, wherein the first bore has a diameter larger than the first head such that a gap is created therebetween.

27. The bone anchoring device according to claim 19, wherein the receiving member is a plate.

28. The bone anchoring device according to claim 19, wherein the receiving member has a cut-out for receiving a rod.

29. A method of using a bone anchoring device, the method comprising:
inserting a first head of an anchoring element in a bore of a second head, the anchoring element comprising a shaft, the first head being directly fixed to the shaft;
inserting the second head in a recess of a receiving member, the second head being pivotally arranged relative to the receiving member, the first head being located in the second head;
attaching the shaft of the anchoring element to a bone;
fixing the second head from pivoting in the recess of the receiving member with a first securing element;
wherein an elastic pressure element is configured to pivotally couple the anchoring element, including the first head and the shaft, and the second head between a first position and a plurality of second positions angularly offset from the first position; and
wherein when the second head is fixed from pivoting in the recess of the receiver member, the first head and the shaft are together pivotable relative to the second head between the first position and the plurality of second positions with the elastic pressure element biasing the first head and the shaft from the plurality of second positions wherein the elastic pressure element is compressed on one side more than an opposite side to the first position wherein the compressive forces exerted on the the elastic pressure element are balanced to provide a resting position of the first head and the shaft in the first position.

30. A method according to claim 29, further comprising inserting a second pressure element in the receiving member, the second pressure element configured to fix the second head in the receiving member in a fixed position relative to the receiving member upon tightening of the first securing element.

31. A method according to claim 29, further comprising inserting a rod in a corresponding recess of the receiving member, and securing the rod in the receiving member with a second securing element.

32. A method according to claim 29, wherein the elastic pressure element is separate from the first head, the elastic pressure element coupling to the first head.

33. A method according to claim 29, wherein the elastic pressure element is integrally constructed with the first head.

34. A bone anchoring device, comprising:
an anchoring element having a shank with a first head directly fixed to the shank;
a receiving member having a recess; and
a second head in the recess of the receiving member and pivotably arranged relative to the receiving member, the first head located in the second head;
at least one securing element, wherein the securing element is moveable from a first securing element position wherein the second head is pivotable in the recess of the receiving member to a second securing element position wherein the second head is rigidly fixed from pivoting in the recess of the receiving member;
an elastic pressure element elastically fixing the first head in a first position to the receiving member when the second head is rigidly fixed from pivoting in the recess of the receiving member in the second securing element position;
wherein the elastic pressure element biases the first head toward the first position from a plurality of second positions angularly offset from the first position; and
wherein the pressure element is less compressed in the first position than in the second position.

* * * * *